United States Patent [19]

Goodbrand

[11] Patent Number: 5,648,539
[45] Date of Patent: Jul. 15, 1997

[54] LOW TEMPERATURE ARYLAMINE PROCESSES

[75] Inventor: H. Bruce Goodbrand, Hamilton, Canada

[73] Assignee: Xerox Corporation, Stamford, Conn.

[21] Appl. No.: 607,953

[22] Filed: Feb. 29, 1996

[51] Int. Cl.$^6$ .................................................. C07C 209/10
[52] U.S. Cl. .................................... 564/309; 564/405
[58] Field of Search ........................... 564/309, 405

[56] References Cited

U.S. PATENT DOCUMENTS

| | | | |
|---|---|---|---|
| 4,265,990 | 5/1981 | Stolka et al. | 430/59 |
| 4,299,983 | 11/1981 | Martin et al. | 564/394 |
| 4,764,625 | 8/1988 | Turner et al. | 548/442 |
| 4,801,517 | 1/1989 | Frechet et al. | 430/59 |

*Primary Examiner*—Richard L. Raymond
*Attorney, Agent, or Firm*—E. O. Palazzo

[57] ABSTRACT

A process for the preparation of arylamines which comprises the reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° C. to about 150° C.

43 Claims, No Drawings

LOW TEMPERATURE ARYLAMINE PROCESSES

BACKGROUND OF THE INVENTION

This invention is generally directed to processes for the preparation of arylamines, triarylamines, charge transporting components, and intermediates for charge transporting molecules and polymers, which intermediates can be selected for the preparation of Verde film components, and more specifically, the present invention relates to an improved process for the preparation of hole transporting molecules, such as arylamines, and wherein there are selected certain copper catalysts, and in embodiments low temperatures. The catalysts selected for the processes of the present invention include ligated copper salts, and more specifically, copper (1) salts, and wherein the ligands are characterized as monodentate tertiary amines and bidentate tertiary amines, such as 1,10-phenanthroline, or pyridine, and the like. The products obtained, such as the arylamines and other charge transporting molecules, with the processes of the present invention can be incorporated into layered photoconductive imaging members with a photogenerating layer and a supporting substrate, reference for example U.S. Pat. No. 4,265,990, the disclosure of which is totally incorporated herein by reference. The aforementioned layered photoconductive imaging members can be negatively charged when the photogenerating layer is situated between the charge transport layer and the substrate, or positively charged when the charge transport layer is situated between the photogenerating layer and the supporting substrate. The layered photoconductive imaging members can be selected for a number of different known imaging and printing processes including, for example, electrophotographic imaging processes, especially xerographic imaging and printing processes wherein negatively charged or positively charged images are rendered visible with toner compositions of the appropriate charge. Generally, these imaging members are sensitive in the wavelength regions of from about 500 to about 850 nanometers, thus diode lasers can be selected as the light source.

Processes for the preparation of certain charge transporting molecules are known, reference for example U.S. Pat. Nos. 4,299,983; 4,485,260; 4,240,987; 4,764,625 and 4,299,983, the disclosures of each of these patents being totally incorporated herein by reference. These and other prior art illustrate the Ullmann condensation of 3-methyldiphenylamine and diiodobiphenyl at high temperatures, for example 160° C., reference the U.S. Pat. No. 4,764,625, and wherein cuprous oxide catalysts are selected. With these processes, the crude charge transport molecules generated are of lower quality and possess lower purity than the charge transport molecules obtained with the processes of the present invention. Higher crude purities enable a much wider choice of purification protocols. As a general rule, high temperature reactions are more prone to produce troublesome impurities necessitating extensive purification. This becomes particularly important when products with electronic grade purities are required, such as for use as charge transporting molecules in layered photoconductive xerographic imaging members, reference U.S. Pat. No. 4,265,990, the disclosure of which is totally incorporated herein by reference. Moreover, lower temperatures have a positive influence on the economics of these processes primarily because of reduced energy demands.

SUMMARY OF THE INVENTION

Examples of objects of the present invention include in embodiments the following.

It is an object of the present invention to provide processes for the preparation of polymer intermediates and small molecules, such as charge transport arylamines with many of the advantages illustrated herein, and wherein the intermediates can be selected for the preparation of charge transporting, especially hole transporting components in layered photoconductive imaging members.

It is yet another object of the present invention to provide low temperature processes for the preparation of charge transport components.

Another object of the present invention resides in the preparation of charge transport components by the Ullmann condensation reaction, and wherein organic ligands of copper are selected as catalyst adjuvants, or catalyst accelerators.

Further, in another object of the present invention there are provided economically scalable processes for the preparation of polymer intermediates and small molecules, and processes for the preparation of arylamines.

Another object of the present invention relates to processes wherein there can be selected lower temperatures for the synthesis of charge transport components by Ullmann amine condensations, for example in the preparation of N,N'-diphenyl-N,N'-bis(3-methylphenyl)-1,1'-biphenyl-4,4'-diamine from about 100° C. to about 150° C., and preferably from about 120° C. to about 130° C., in the preparation of N,N'-diphenyl-N,N'-bis(3-methoxyphenyl)-1,1'-biphenyl-4,4'-diamine from about 130° C. to about 150° C. and preferably from about 135° C. to about 140° C., in the general preparation of triarylamines from about 100° C. to about 150° C. and preferably from about 120° C. to about 130° C., and more specifically, wherein organic ligands of copper are selected as a catalyst accelerator, wherein the reaction is accomplished in the presence of a hydroxide, such as potassium hydroxide and hydrocarbon solvents like toluene or xylene, and wherein the crude product obtained is of excellent purity, and which components or products may be further purified by known methods, such as filtration, distillation, column chromatography, vacuum distillation, and the like.

A further specific object of the present invention resides in the provision of photoresponsive imaging members with an arylamine hole transport layer obtained by the processes illustrated herein, and a photogenerator layer.

Moreover, in another object of the present invention there are provided processes for the preparation of hole transporting molecules wherein the temperature of the reaction is lower than the about 160° C. presently utilized for the preparation of certain commercial hole transporting arylamines, and more specifically, wherein the invention reaction in embodiments can be accomplished, for example, at temperatures 40° lower than 160° C., and yet more specifically at 125° C.; and also wherein novel catalysts, such as the product of cuprous chloride, and a 1,10-phenanthroline chelating agent is selected as a catalyst. The aforementioned lower temperature, milder reaction conditions enable, it is believed, simpler processes, and more efficient protocols for the preparation of pure, that is for example electronic grade, arylamines.

Furthermore, in another object of the present invention there are provided low temperature processes for the preparation of monomers that can be selected as intermediates for the preparation of hole transporting components, and hole transporting polymers.

Further, in another object of the present invention in embodiments thereof there may be enabled, it is believed, processes for the preparation of oligomers, polymers, intermediates, and the like.

These and other objects of the present invention can be accomplished in embodiments thereof by the provision of processes for the preparation of aryl amines, and more specifically, intermediates for charge transporting polymers, and charge transport arylamines, or tertiary amines. In embodiments, the process of the present invention relates to the preparation of hole transport amines as illustrated in U.S. Pat. No. 4,764,625, the disclosure of which is totally incorporated herein by reference, and which process comprises the Ullmann condensation of 3-methyldiphenylamine (3-MDA) and diiodobiphenyl (DIB) with certain copper catalysts in the presence of an organic solvent and a hydroxide, and wherein the condensation is accomplished at a low temperature of, for example, from about 100° C. to about 150° C., and preferably from about 120° C. to about 140° C., and more preferably at about 125° C.

Embodiments of the present invention include a process which comprises the accelerated reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° C. to about 150° C.; Ullmann condensation process for the preparation of arylamines, which comprises the reaction of 3-methyldiphenylamine and diiodobiphenyl in the presence of an organic solvent, an alkali metal, and a copper containing organic ligand, and wherein the ligand is selected from the group consisting of monodentate tertiary amines and bidentate tertiary amines, and which reaction is accomplished at a temperature of from about 120° C. to about 150° C.; a process comprising the accelerated reaction of 3-methoxydiphenylamine and diiodobiphenyl in the presence of a ligated copper catalyst and wherein the organic ligand is selected from bidentate amines, monodentate amines, or mixtures thereof, and which process is accomplished at a reaction temperature of from about 135° C. to about 140° C.; and a process which comprises the reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° C. to about 150° C. Also, embodiments of the present invention include a catalyst comprised of a copper containing organic ligand, and wherein the ligand is selected from the group consisting of monodentate tertiary amines, and bidentate tertiary amines, and more specifically, wherein the ligand is selected from the group consisting of 1,10-phenanthroline and pyridine; processes wherein the catalyst is 1,10-phenanthrolato copper (1) (monovalent) chloride, dipyridino copper (1) chloride, 1,10-phenanthrolato copper (1) bromide, dipyridino copper (1) bromide, 1,10-phenanthrolato copper (1) chloride, 1,10-phenanthrolato copper (1) bromide, and dipyridino copper (1) bromide; a process for the preparation of triarylamines, which comprises the reaction of an aniline and a halotoluene, or halobenzene in the presence of a ligated copper catalyst, and wherein the ligand is selected from the group consisting of monodentate tertiary amines, and bidentate tertiary amines, and which reaction is accomplished at a temperature of from about 120° C. to about 150° C., and preferably to about 135° C.; a process for the preparation of triarylamines, which comprises the reaction of an aniline and an excess amount of a halogenated aromatic, such as a halobenzene, or a halotoluene in the presence of a ligated copper catalyst and wherein the ligand is selected from the group consisting of monodentate tertiary amines and bidentate tertiary amines, and which reaction is accomplished at a temperature of from about 125° C. to about 140° C., and preferably to about 130° C.; a process for the preparation of triarylamines, which comprises the reaction of an aniline and an excess amount of a halobenzene in the presence of a ligated copper catalyst, and wherein the ligand is selected from the group consisting of monodentate tertiary amines and bidentate tertiary amines, and which reaction is accomplished at a temperature of from about 125° C. to about 130° C.; a process wherein the aniline is a haloaniline, the aniline is aniline, the aniline is a bromoaniline, the aniline is 4-bromoaniline, the aniline is a chloroaniline, the aniline is a fluoroaniline, or iodoaniline; a process wherein the aniline is an alkyl aniline wherein the alkyl of said aniline has, for example, from 1 to about 20 carbon atoms, or aryl aniline wherein the aryl of said substituted aniline has, for example, from 6 to about 24 carbon atoms, the halobenzene is iodotoluene, the halobenzene is paraiodobenzene, and the halobenzene is an alkyl substituted halobenzene; a process wherein the triarylamine product contains two identical substituents; a process wherein for each equivalent (or mole) of aniline there are utilized from about 2 to about 4 equivalents of the halobenzene reactant and about 0.1 to 0.5 equivalents of the ligated copper catalyst; a process wherein the reaction is accomplished in the presence of a hydrocarbon solvent of toluene or xylene; a process wherein the arylamine product is bis(p-methylphenyl)-p-bromophenylamine, bis(phenyl)-p-methylphenyl amine, bis(p-chlorophenyl)-p-methylamine, bis(p-bromophenyl)-p-methylphenylamine, or bis(p-methylphenyl)phenylamine; a process wherein for each equivalent (or mole) of aniline there are utilized from about 2.1 to about 2.2 equivalents of the halobenzene reactant and from about 0.5 to about 0.15 equivalents of the ligated copper catalyst; a process wherein for each equivalent (or mole) of aniline there are utilized 2 to 4 equivalents of the halobenzene reactant and 0.1 to 0.5 equivalents of the ligated copper catalyst; a process for the preparation of an arylamine comprising the accelerated reaction of 3-methoxydiphenylamine and diiodobiphenyl in the presence of a ligated copper catalyst, and wherein the organic ligand is a bidentate amine or a monodentate amine, and which process is accomplished at a reaction temperature of from about 130° C. to about 140° C.; a process which comprises the reaction of methyldiphenylamine and diiodobiphenyl in the presence of a ligated copper catalyst, and wherein the ligand is selected from the group consisting of monodentate tertiary amines, and bidentate tertiary amines, and which reaction is accomplished at a temperature of from about 120° C. to about 150° C.; a process for the preparation of arylamines, or aryloxyamines, which comprises the reaction of methyldiphenylamine or alkoxy like methoxydiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° C. to about 150° C.; a process wherein the reaction temperature is 140° C. and there is formed an alkoxyamine; a process for the preparation of arylamines, which comprises the heating of methyldiphenylamine and diiodobiphenyl in the presence of a ligated copper catalyst, and wherein the ligand is selected from the group consisting of monodentate tertiary amines and bidentate tertiary amines; a catalyst comprised of a copper containing organic ligand, and wherein the ligand is selected from the group consisting of monodentate tertiary amines and bidentate tertiary amines; and copper catalysts or compounds of the formulas

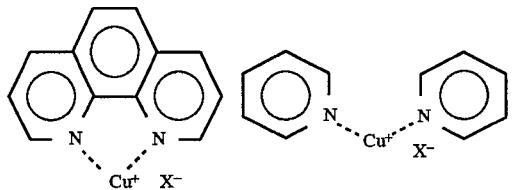

wherein X— is a halide, such as chloride.

The catalyst selected for the processes of the present invention is as illustrated herein, and in embodiments is comprised of ligated copper salts, including the halide salts, such as chloride, bromide, iodide, and fluoride, especially copper (1), and wherein the ligands are monodentate tertiary amines, or bidentate tertiary amines, such as 1,10-phenanthroline or pyridine. The amount of catalyst selected can vary, and generally, the catalyst is employed in effective amounts, such as from about 1 to about 20 mole percent of the reactants, and preferably from about 5 to about 12 mole percent of the limiting reactant. Examples of postulated formula structures for the copper catalysts include

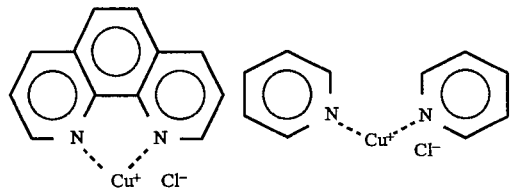

and in embodiments wherein the catalyst is 1,10-phenanthrolato copper (1) chloride, dipyridino copper (1) chloride, 1,10-phenanthrolato copper (1) bromide, or dipyridino copper (1) bromide, and the like.

The catalysts can be prepared as illustrated herein, and more specifically, by the reaction of a copper salt like cuprous chloride with the appropriate ligand like 4,4'-diiodobiphenyl, and which reaction is accomplished with heating, for example, from about 70° C. to about 125° C. The reaction mixture is cooled and the product catalyst may, it is believed, be isolated by, for example, filtration. Preferably, the catalyst is prepared in situ, as illustrated in the Examples, during its use in the processes of the present invention when, for example, arylamines are generated.

Embodiments of the present invention include:

A process which comprises the reaction of an arylamine or diarylamine with a haloaromatic or dihaloaromatic, and more specifically, the reaction of methyldiphenylamine and diiodobiphenyl in the presence of a ligated copper catalyst, and wherein the ligand is selected from the group consisting of monodentate tertiary amines and bidentate tertiary amines, and more specifically, 1,10-phenanthroline, biquinolyl, pyridine, sparteine, 2,2'-dipyridyl, dimethylglyoxime, N,N'-tetramethylethylene diamine (EDTA), N,N'-tetramethyl-1,8-diaminonaphthalene, and the like, and which reaction is accomplished at a temperature of from about 120° C. to about 150° C., followed by cooling, and wherein the product was identified by analytical methods, such as high performance liquid chromatography. The product purity in embodiments is as indicated herein and, more specifically, is from about 97 to about 99 percent pure as determined by HPLC, that is high performance liquid chromatography. Examples of diarylamines selected include 3-methyl diphenylamine and 3-methoxy diphenylamine, and halo- and dihaloaromatic components include 4,4'-diiodobiphenyl and 4-iodotoluene. Either reagent, or reactant can be used in excess. For the preparation of arylamines, such as the substituted benzidine species, the diarylamine is employed, for example, in excesses ranging from about 1 to about 100 percent molar excess with a preferred range of from about 10 to about 20 percent excess. For the general preparation of triarylamine species, the haloaromatic component is used, for example, in a range amount of about 10 to about 50 percent molar excess with the preferred range being 10 to 25 percent molar excess.

Examples of products obtained include the arylamine charge transport molecules illustrated herein like N,N'-diphenyl-bis(3-methylphenyl)-1,1'-biphenyl-4,4'diamine, and the like; the charge transporting intermediate N,N'-diphenyl-bis(3-methoxyphenyl)-1,1'-biphenyl-4,4'-diamine, and the like; and the charge transporting triarylamines bis(p-methylphenyl)-p-bromophenylamine and bis(p-methylphenyl)phenylamine, and the like.

For the synthesis of tetraphenylbenzidine type components or species, such as N,N'-diphenyl-N,N'-bis(3-methylphenyl)-1,1'-biphenyl-4,4'-diamine and N,N'-diphenyl-N,N'-bis(3-methoxyphenyl)-1,1'-biphenyl-4,4'-diamine, the following was accomplished.

In an appropriate reaction flask equipped for mechanical stirring and fitted with an inert gas purge and a Dean-Stark trap under a reflux condenser is placed in the following order:

1 mole of a 4'4'-dihalobiphenyl, preferably the diiodo derivative, 2 to 6 moles, preferably 2 to 4 moles of the diphenyl or substituted diphenylamine component, with 4 moles of 3-methyldiphenylamine being especially preferred for the methyl derivative, and 2.2 moles of 3-methoxydiphenylamine for the methoxy derivative;

5 to 10 moles, preferably 7 to 8 moles of a hydrocarbon, mixed hydrocarbon or aromatic hydrocarbon solvent, such as toluene, mixed xylenes, dodecane or the like, and wherein toluene is preferred for the methyl derivative, and xylene for the methoxy derivative;

0.01 to 0.25 mole, preferably 0.05 to 0.15 mole of a copper (1) salt catalyst (chloride, bromide acetate, and the like);

an equal molar amount (relative to the copper salt) of a copper (1) catalyst with a bidentate amine ligand, preferably 1,10-phenanthroline, or with respect to the monodentate ligand preferably pyridine, a double molar excess relative to the copper salt, is added; and 5 to 13 moles, preferably 7 to 10 moles of potassium hydroxide flake are added. The reaction mixture is then heated rapidly to reflux under an inert argon atmosphere and maintained at that temperature, preferably 125° for the methyl derivative, and preferably 140° for the methoxy derivative while water is removed by azeotropic distillation. When chromatographic analysis confirms complete reaction, generally 4 to 8 hours, typically 5 hours, 6 moles of toluene and 6 moles of deionized water are added to quench the reaction and an equimolar amount of glacial acetic acid (relative to added potassium hydroxide) is added to achieve reaction neutrality. The reaction mixture can then be transferred to a separatory funnel, the layers separated, and the organic phase additionally washed with two further 6 mole portions of deionized water. The warm (80° C.) organic phase is slurry treated with 30 to 100 grams, preferably 40 to 60 grams of Alcoa CG-20 Alumina for 30 minutes, and the alumina removed by filtration. Half of, that is 50 parts, or 50 percent, of the organic solvent is then removed by distillation under an inert atmosphere and replaced by the addition of an equal amount of ISOPAR M™ solvent. Slow cooling causes the product to precipitate, and which product is isolated or is secured by filtration. Yields range from 89 to 90 percent in the above process situation embodiments.

For the general synthesis of triarylamines in which all aryl groups are identically substituted, or in which one of the aryl groups possesses a different substitution pattern, the following was accomplished.

In a suitable reaction flask are placed 50 millimoles of aniline, or a substituted aniline, 100 to 500 millimoles, preferably 100 to 150 millimoles of a haloaromatic or substituted haloaromatic compound, 0.1 to 0.5 mole, preferably 0.2 to 0.3 mole of an aromatic or hydrocarbon solvent, preferably xylene, 1 to 25 millimoles, preferably 5 to 10 millimoles of the copper (1) salt catalyst, chloride, bromide, acetate, and the like, an equimolar amount (relative to the copper salt) of a bidentate amine ligand, preferably 1,10-phenanthroline, or with respect to a monodentate ligand, preferably pyridine, a double molar excess relative to the copper salt is added. In a similar manner as illustrated herein, the reaction is heated to a temperature of about 125° C. for 5 hours to complete the reaction. Washing and alumina treatment as illustrated herein are then accomplished, followed by the rotary evaporation of solvent to provide the desired triaryl amine product.

Examples of charge transport amines generated with the processes of the present invention include those as illustrated in U.S. Pat. No. 4,764,625, the disclosure of which is totally incorporated herein by reference, such as molecules of the following formula

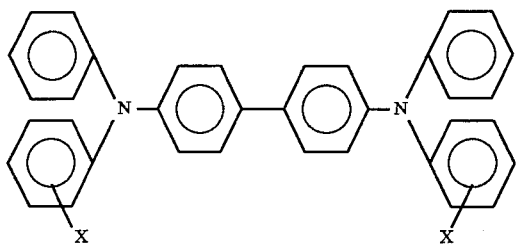

wherein X is hydrogen, alkyl or a halogen, especially those substituents selected from the group consisting of (ortho) CH$_3$, (para) CH$_3$, (ortho) Cl, (meta) Cl, and (para) Cl. Examples of specific arylamines generated with the processes of the present invention include N,N'-diphenyl-N,N'-bis(alkylphenyl)-1,1'-biphenyl-4,4'-diamine wherein alkyl is selected from the group consisting of methyl, such as 2-methyl, 3-methyl and 4-methyl, ethyl, propyl, butyl, hexyl, and the like. With chloro substitution, the amine is N,N'-diphenyl-N,N'-bis(halo phenyl)-1,1'-biphenyl-4,4'-diamine wherein halo is 2-chloro, 3-chloro, or 4-chloro. Specific amines generated with the processes of the present invention in embodiments are N,N'-diphenyl-N,N'-bis(3-methylphenyl)-1,1'-biphenyl-4,4'-diamine, N,N'-diphenyl-N,N'-bis(3-methylphenyl)-(p-terphenyl)-4,4'-diamine, N,N'-diphenyl-N,N'-bis(3-methylphenyl)-pyrenyl-1,6-diamine, N,N'-diphenyl-N,N'-bis(3-methylphenyl)-1,4-phenylenediamine, and N,N'-tetra(p-methylphenyl)-1,4-biphenyl-4,4'-diamine. Other known charge transport molecules can be prepared, reference for example U.S. Pat. Nos. 4,921,773 and 4,464,450, the disclosures of which are totally incorporated herein by reference.

Numerous different layered photoresponsive imaging members containing the charge transporting amines generated with the process of the present invention can be provided. In embodiments, thus the layered photoresponsive imaging members are comprised of a supporting substrate, a charge transport layer, especially an arylamine hole transport layer obtained with the process of the present invention, and situated therebetween a photogenerator layer comprised, for example, of phthalocyanines, hydroxygallium phthalocyanines, especially Type V, titanyl phthalocyanines, perylenes, especially BZP, selenium, especially trigonal selenium, selenium alloys, and the like, including other effective known photogenerating pigments. Another embodiment of the present invention is directed to positively charged layered photoresponsive imaging members comprised of a supporting substrate, a charge transport layer, especially an arylamine hole transport layer, and as a top overcoating a photogenerating layer. Moreover, there is provided in accordance with the present invention an improved negatively charged photoresponsive imaging member comprised of a supporting substrate, a thin adhesive layer, a photogenerator layer dispersed in a polymeric resinous binder, and as a top layer arylamine hole transporting molecules dispersed in a polymeric resinous binder, and which arylamine molecules are obtained with the processes of the present invention.

The photoresponsive imaging members can be prepared by a number of known methods, the process parameters, and the order of coating of the layers being dependent on the member desired. The imaging members suitable for positive charging can be prepared by reversing the order of deposition of photogenerator and hole transport layers. The photogenerating and charge transport layers of the imaging members can be coated as solutions or dispersions onto selective substrates by the use of a spray coater, dip coater, extrusion coater, roller coater, wire-bar coater, slot coater, doctor blade coater, gravure coater, and the like, and dried at from 40° C. to about 200° C. for from 10 minutes to several hours, and more specifically, about 5 hours under stationary conditions or in an air flow. The coating is accomplished to provide a final coating thickness of from 0.01 to about 30 microns after it has dried. The fabrication conditions for a given layer can be tailored to achieve optimum performance and cost in the final device. The imaging members are useful in xerographic imaging processes wherein, for example, when the pigment is a titanyl phthalocyanine pigment, it absorbs light of a wavelength of from about 600 nanometers to about 900 nanometers. In these known processes, electrostatic latent images are initially formed on the imaging member, followed by development, and thereafter, transferring and fixing the image to a suitable substrate, such as paper. Moreover, the imaging members can be selected for electronic printing processes with gallium arsenide light emitting diode (LED) arrays which typically function at wavelengths of from 660 to about 830 nanometers.

Substrate layers selected for the imaging members can be opaque or substantially transparent, and may comprise any suitable material having the requisite mechanical properties. Thus, the substrate may comprise a layer of insulating material including inorganic or organic polymeric materials, such as MYLAR® a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass, or the like. The substrate may be flexible, seamless, or rigid and many have a number of many different configurations, such as for example a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as for example polycarbonate materials commercially available as MAKROLON®.

The thickness of the substrate layer depends on many factors, including economical considerations, thus this layer may be of substantial thickness, for example over 3,000 microns, or of minimum thickness providing there are no adverse effects on the system. In one embodiment, the thickness of this layer is from about 75 microns to about 300 microns.

Generally, the thickness of the photogenerator layer depends on a number of factors, including the thicknesses of the other layers and the amount of photogenerator material contained in this layer. Accordingly, this layer can be of a thickness of from about 0.05 micron to about 10 microns when the photogenerator composition layer is present in an amount of from about 5 percent to about 100 percent by volume. In one embodiment, this layer is of a thickness of from about 0.25 micron to about 1 micron when the photogenerator composition is present in this layer in an amount of 30 to 75 percent by volume. The maximum thickness of this layer in an embodiment is dependent primarily upon factors, such as photosensitivity, electrical properties and mechanical considerations. The charge generator layer can be obtained by dispersion coating the photogenerating pigment, and a binder resin with a suitable solvent. The binder may be omitted. The dispersion can be prepared by mixing and/or milling the photogenerating pigment in equipment such as paint shakers, ball mills, sand mills and attritors. Common grinding media, such as glass beads, steel balls or ceramic beads, may be used in this equipment. The binder resin may be selected from a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. The solvents to dissolve these binders or resins depend upon the particular resin. In embodiments, it is desirable to select solvents that do not effect the other coated layers of the device. Examples of useful solvents are ketones, alcohols, aromatic hydrocarbons, halogenated aliphatic hydrocarbons, ethers, amines, amides, esters, and the like. Specific solvent examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethylformamide, dimethylacetamide, butyl acetate, ethyl acetate, methoxyethyl acetate, and the like.

The coating of the photogenerating pigment dispersion can be accomplished with spray, dip or wire-bar methods such that the final dry thickness of the charge generator layer is from 0.01 to 30 microns and preferably from 0.1 to 15 microns after being dried at 40° C. to 150° C. for 5 to 90 minutes.

Illustrative examples of polymeric binder resinous materials that can be selected for the photogenerator pigment include those polymers as disclosed in U.S. Pat. No. 3,121, 006, the disclosure of which is totally incorporated herein by reference.

As adhesives usually in contact with the supporting substrate, there can be selected various known substances inclusive of polyesters, polyamides, poly(vinyl butyral), poly(vinyl alcohol), polyurethane and polyacrylonitrile. This layer is of a thickness of from about 0.05 micron to about 1 micron. Optionally, this layer may contain conductive and nonconductive particles, such as zinc oxide, titanium dioxide, silicon nitride, carbon black, and the like, to provide, for example, in embodiments of the present invention, desirable electrical and optical properties.

Examples of the highly insulating and transparent resinous material or inactive binder resinous selected for the amine charge transport layer include materials such as those described in U.S. Pat. No. 3,121,006, the disclosure of which is totally incorporated herein by reference. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000, with a molecular weight of from about 50,000 to about 100,000 being particularly preferred. Generally, the resinous binder contains from about 10 to about 75 percent by weight of the active charge transport material, and preferably from about 35 percent to about 50 percent of this material.

Also, included within the scope of the present invention are methods of imaging and printing with the photoresponsive devices illustrated herein. These methods generally involve the formation of an electrostatic latent image on the imaging member, followed by developing the image with a toner composition, reference U.S. Pat. Nos. 4,560,635; 4,298,697 and 4,338,390, the disclosures of which are totally incorporated herein by reference, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The following Examples are being supplied to further define various species of the present invention, it being noted that these Examples are intended to illustrate and not limit the scope of the present invention. Parts and percentages are by weight unless otherwise indicated. Yield and purity were determined by known analytical methods.

EXAMPLE I

N,N'-diphenyl-N,N'-bis(3-methylphenyl)-1,1'-biphenyl-4,4'-diamine can be prepared in the following manner.

A 500 milliliter 3-neck round bottom flask equipped with a mechanical stirrer, reflux condenser, and argon inlet was purged with argon and then charged with the following reagents in the indicated order, all under an argon blanket:

| 3-methyldiphenylamine | 27.06 grams | (148 mmol, 100% molar excess) |
|---|---|---|
| 4,4'-diiodobiphenyl | 15.00 grams | (37 mmol) |
| Toluene | 26.00 grams | |
| 1,10-phenanthroline | 1.15 grams | (6 mmol) |
| Cuprous chloride | 0.63 gram | (6 mmol) |
| KOH flake | 16.56 grams | (295 mmol) |

Under an inert atmosphere of argon, the reaction mixture was quickly heated over a period of 30 minutes to the temperature of reflux (125°) and allowed to proceed at that temperature until chromatographic analysis by high performance liquid chromatography indicated that the reaction was complete after approximately 5 hours. 150 Milliliters of toluene and 150 milliliters of deionized water were then added, and finally 17.7 grams of acetic acid were also added to neutralize the KOH. The resulting warm, 60° C., two phase mixture was transferred to a separatory funnel, and the layers separated. The organic phase was washed with two 100 milliliter portions of deionized water and treated while warm, approximately 45° C., and under argon with 2.0 grams of Alcoa CG-20 alumina. The crude N,N'-diphenyl-N,N'-bis(3-methylphenyl)-1,1'-biphenyl-4,4'-diamine was isolated by filtering off the alumina and distilling toluene. A total of 100 milliliters of toluene was removed in this manner and replaced by 100 milliliters of ISOPAR M™. Slow cooling of the solution under argon afforded the high purity crude product in 92 percent yield after vacuum filtration and drying. The crude purity was 95 percent as evidenced by high performance liquid chromatography.

EXAMPLE II

N,N'-diphenyl-N,N'-bis(3-methoxyphenyl)-1,1-biphenyl-4,4'-diamine was prepared by essentially repeating Example I, however, some different components, and a slightly different reactant stoichiometry were selected.

In a 500 milliliter round bottom flask equipped with mechanical stirrer, thermometer, argon inlet and condenser with attached Dean-Stark trap were charged the following reactants in the order indicated, all under argon:

| | | |
|---|---|---|
| 3-methoxydiphenylamine | 13.16 grams | (66 mmol) |
| 4,4'-diiodobiphenyl | 12.19 grams | (30 mmol) |
| 1,10-phenanthroline | 0.54 gram | (3 mmol) |
| Xylene | | (20 ml) |
| Cuprous Chloride | 0.3 gram | (3 mmol) |
| KOH flake | 13.20 grams | (240 mmol) |

The reaction was rapidly heated over a period of 30 minutes to the temperature of reflux (145° C.) and allowed to proceed at that temperature while the progress of the reaction was monitored by high performance liquid chromatography. After 5 hours, the reaction was deemed to be complete and the heating was discontinued. After the internal temperature had decreased to 100° C., 150 milliliters of toluene and 100 milliliters of deionized water were added and stirring was continued for 10 minutes. To the warm mixture, about 80° C., were cautiously added 23.8 grams of glacial acetic acid to neutralize the added KOH. The resulting mixture was transferred to a separatory funnel, and the organic layer sequentially washed with three 100 milliliters portions of warm, 80° C., deionized water. The workup was then accomplished as described in Example I with preliminary treatments with 5 grams of Filtrol 24, an acid washed clay, and Alcoa CG-20 alumina, followed by filtration, and precipitation in a large excess of heptane to provide the crude product compound in a comparable yield to the standard high temperature reaction. Importantly, no tars were produced as is common in standard prior art reactions. Chromatographic analysis indicates that the crude product was of high purity, 95 percent or greater, in some instances, such as 98 percent, as evidenced by high performance liquid chromatography.

EXAMPLE III

Bis(p-methylphenyl)-p-bromophenylamine:

In a 500 milliliter three-necked flask equipped with a mechanical stirrer, thermometer and Dean-Stark trap, all under an argon atmosphere, were added molten p-iodotoluene (27.3 grams, 125 millimoles), 22 grams of xylene, p-bromoaniline (8.7 grams, 50 millimoles), and 1,10-phenanthroline (1.8 grams, 10 millimoles). The reaction mixture was then heated to 100° C. at which point potassium hydroxide flake (22.4 grams, 400 millimoles) and cuprous chloride (1 gram, 10 millimoles) were added. The temperature was then adjusted to 125° C., and the reaction progress monitored by high performance liquid chromatography. Analysis showed the reaction to be 94 percent complete at 2 hours and 98 percent complete at 5 hours at which point the reaction was terminated. Product isolation was accomplished by adding 24 grams of acetic acid, and partitioning the reaction mixture between 100 grams of toluene and 100 grams of deionized water. The organic phase was further washed several times with deionized water, and the solvent removed to afford 15 grams (84.5 percent) of the desired product of high purity (HPLC, 98 area percent).

In this manner the above triphenylamine bis(p-methylphenyl)-p-bromophenylamine was produced in excellent yield in a short time, free from troublesome impurities, which impurities are present in related prior art high temperature processes.

EXAMPLE IV

Bis(p-methylphenyl)phenyl amine:

In a 500 milliliter three-necked flask fitted with a magnetic stirrer, condenser and argon purge were added p-iodotoluene (27.3 grams, 125 millimoles), aniline (4.7 grams, 50 millimoles), 1,10-phenanthroline (1.8 grams, 10 millimoles), and 22 grams of o-xylene. The solution was heated to 100° C. with stirring at which point cuprous chloride (1.0 gram, 10 millimoles) and potassium hydroxide flake (22.4 grams, 400 millimoles) were added. The reaction temperature was increased to 125° C. and maintained for 6 hours. The reaction was worked up by the addition of 150 milliliters of toluene and 150 milliliters of deionized water, followed by the addition of 24 grams of glacial acetic acid. The organic layer was separated and washed twice with 100 milliliter portions of deionized water. Solvent was removed by rotary evaporation and the resulting solid taken up in 100 milliliters of hexane and treated with 20 grams of neutral alumina for 1 hour. Filtration and evaporation of solvent provided 9.8 grams (72 percent) of yellow crystals, mp 103°0 to 105° C. Proton and carbon-13 nmr spectra confirm the anticipated structure and evidence a purity of 98 percent.

A number of other compounds can be prepared in accordance with the present invention by repeating the above processes with different reactants, and it is believed that substantially similar results with regard to purity and yield will be obtained at the low temperatures used. Also, other copper catalysts illustrated herein can be selected to obtain arylamines and other products as illustrated herein, and wherein the purity thereof will be high, it is believed, for example 95 percent, and wherein temperatures of, for example, 40° lower than related prior art processes, that is for example 120° C., can be selected.

Other modifications of the present invention may occur to those skilled in the art subsequent to a review of the present application and these modifications, including equivalents thereof, are intended to be included within the scope of the present invention.

What is claimed is:

1. A process for the preparation of arylamines which comprises the reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° C. to about 150° C.

2. A process in accordance with claim 1 wherein the copper is copper (1).

3. A process in accordance with claim 1 wherein said ligand is selected from the group consisting of 1,10-phenanthrolinepyridine and pyridine, and wherein the temperature of the reaction is from about 120° C. to about 140° C.

4. A process in accordance with claim 3 wherein the temperature of the reaction is about 125° C.

5. A process in accordance with claim 1 wherein said reaction is accomplished in the presence of an alkali metal hydroxide and an organic solvent.

6. A process in accordance with claim 5 wherein the hydroxide is potassium hydroxide, and the solvent is toluene.

7. A process in accordance with claim 1 wherein said methyldiphenylamine is 3-methyldiphenylamine.

8. A process in accordance with claim 2 wherein said methyldiphenylamine is 3-methyldiphenylamine.

9. A process in accordance with claim 4 wherein said methyldiphenylamine is 3-methyldiphenylamine.

10. A process in accordance with claim 5 wherein said methyldiphenylamine is 3-methyldiphenylamine.

11. An Ullmann condensation process for the preparation of arylamines consisting essentially of the reaction of 3-methyldiphenylamine and diiodobiphenyl in the presence of an organic solvent, an alkali metal hydroxide, and a copper containing organic ligand catalyst, and wherein the ligand is selected from the group consisting of monodentate tertiary amines, and bidentate tertiary amines, and which reaction is accomplished at a temperature of from about 120° C. to about 150° C., and wherein said copper catalyst is of the following alternative formulas

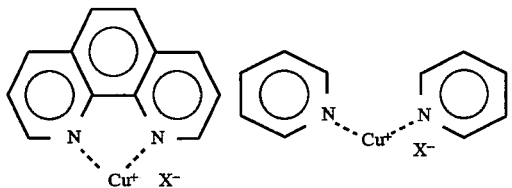

and wherein X– is a halide.

12. A process in accordance with claim 11 wherein the copper is copper (1).

13. A process in accordance with claim 11 wherein said ligand is 1,10-phenanthroline, or pyridine.

14. A process in accordance with claim 11 wherein said copper catalyst is a 1,10-phenanthrolato-copper (1) salt.

15. A process in accordance with claim 11 wherein said copper catalyst is a dipyridino copper (1) salt.

16. A process in accordance with claim 11 wherein said hydroxide is potassium hydroxide, and said solvent is the organic solvent toluene.

17. A process in accordance with claim 11 wherein from about 2 to about 4 molar excess of the diphenylamine component is utilized.

18. A process in accordance with claim 11 wherein the purity of the arylamine product is from about 70 to about 95 percent.

19. A process in accordance with claim 18 wherein the product is further purified, and wherein the purity of the resulting product is from about 95 to about 99 percent.

20. A process in accordance with claim 18 wherein the product is further purified by column chromatography.

21. A process in accordance with claim 1 wherein the arylamine product is of the formula

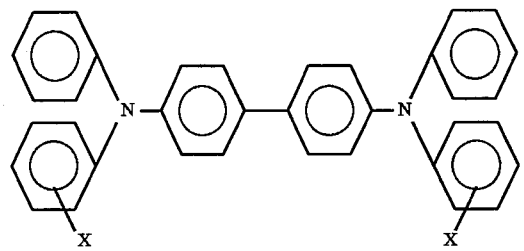

wherein X is hydrogen, alkyl or a halogen.

22. A process in accordance with claim 11 wherein X is selected from the group consisting of (ortho) $CH_3$, (para) $CH_3$, (ortho) Cl, (meta) Cl, and (para) Cl.

23. A process in accordance with claim 21 wherein the arylamine product is N,N'-diphenyl-N,N'-bis(alkylphenyl)-1,1-biphenyl-4,4'-diamine.

24. A process in accordance with claim 21 wherein the arylamine product is N,N'-diphenyl-N,N'-bis(3-methylphenyl)-1,1'-biphenyl-4,4'-diamine.

25. A process in accordance with claim 15 wherein the arylamine product is N,N'-diphenyl-N,N'-bis(3-methylphenyl)-1,1'-biphenyl-4,4'-diamine.

26. A process in accordance with claim 16 wherein the arylamine product is N,N'-diphenyl-N,N'-bis(3-methylphenyl)-1,1'-biphenyl-4,4'-diamine.

27. A process in accordance with claim 11 wherein said temperature of the reaction is from about 120° C. to about 130° C.

28. A process for the preparation of an arylamine comprising the accelerated reaction of 3-methoxydiphenylamine and diiodobiphenyl in the presence of a ligated copper catalyst, and wherein the organic ligand is selected from the group consisting of bidentate tertiary amines and monodentate tertiary amines, and which process is accomplished at a reaction temperature of from about 120° C. to about 140° C.

29. A process which comprises the reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° to about 150° C., and wherein said catalyst is of the following alternative formulas

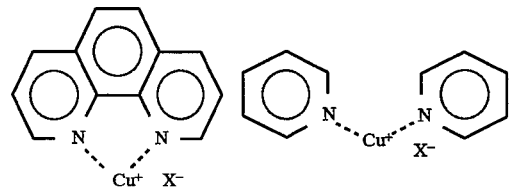

and wherein X– is a halide.

30. A process for the preparation of arylamines consisting essentially of the reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 120° C. to about 150° C.

31. A process in accordance with claim 30 wherein the reaction temperature is 140° C., and there is formed an alkoxyamine.

32. A process for the preparation of arylamines which comprises the heating of methyldiphenylamine and diiodobiphenyl in the presence of a ligated copper catalyst, and wherein the ligand is selected from the group consisting of monodentate tertiary amine, and bidentate tertiary amines.

33. A process in accordance with claim 32 wherein said copper catalyst is 1,10-phenanthrolato-copper (1) chloride.

34. A process in accordance with claim 32 wherein said copper catalyst is 1,10-phenanthrolato-copper (1) bromide.

35. A process in accordance with claim 32 wherein said copper catalyst is 1,10-phenanthrolato-copper (1) iodide, or 1,10-phenanthrolato-copper (1) fluoride.

36. A process in accordance with claim 32 wherein said copper catalyst is dipyridino-copper (1) chloride.

37. A process in accordance with claim 32 wherein said copper catalyst is dipyridino-copper (1) bromide.

38. A process in accordance with claim 32 wherein said copper catalyst is dipyridino-copper (1) iodide, or dipyridino-copper (1) fluoride.

39. A process consisting essentially of the reaction of methyldiphenylamine and diiodobiphenyl in the presence of a ligated copper catalyst, and wherein the ligand is selected from the group consisting of monodentate tertiary amines and bidentate tertiary amines, and which reaction is accomplished at a temperature of from about 100° to about 150° C.

40. A process in accordance with claim 39 wherein the reaction is accomplished at a temperature of from about 120° to about 150° C.

41. A process in accordance with claim 39 wherein said ligated copper catalyst is of the formula

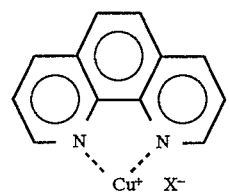

wherein X− is a halide.

42. A process in accordance with claim 39 wherein said ligated copper catalyst is of the formula

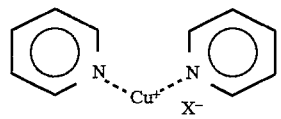

wherein X− is a halide.

43. A process in accordance with claim 1 wherein said copper catalyst is selected from the group consisting 1,10-phenanthrolato copper (1) (monovalent) chloride, dipyridino copper (1) chloride, 1,10-phenanthrolato copper (1) bromide, dipyridino copper (1) bromide, 1,10-phenanthrolato copper (1) chloride, 1,10-phenanthrolato copper (1) bromide, and dipyridino copper (1) bromide.

* * * * *